(12) United States Patent
Levy

(10) Patent No.: US 6,506,961 B1
(45) Date of Patent: Jan. 14, 2003

(54) LIGHT INCONTINENT PRODUCT

(75) Inventor: Ruth Levy, Collegeville, PA (US)

(73) Assignee: Tyco Healthcare Retail Services AG (CH)

(*) Notice: Subject to any disclaimer, the term of this patent is extended or adjusted under 35 U.S.C. 154(b) by 41 days.

(21) Appl. No.: 09/624,088

(22) Filed: Jul. 24, 2000

(51) Int. Cl.[7] .............................................. A61F 13/15
(52) U.S. Cl. ................. 604/380; 604/382; 604/385.101
(58) Field of Search .................................. 604/378, 379, 604/380, 385.01, 385.21, 385.23, 385.101

(56) References Cited

U.S. PATENT DOCUMENTS

| | | | |
|---|---|---|---|
| 2,890,700 A | * 6/1959 | Lonberg-Holm | 128/284 |
| 4,624,666 A | 11/1986 | DeRossett et al. | |
| 4,752,349 A | * 6/1988 | Gebel | 156/267 |
| 4,758,240 A | 7/1988 | Glassman | |
| 4,790,838 A | * 12/1988 | Pignuel et al. | 604/366 |
| 4,869,724 A | * 9/1989 | Scripps | 604/389 |
| 5,092,860 A | 3/1992 | Pigneul | |
| 5,104,396 A | 4/1992 | Oatley et al. | |
| 5,447,506 A | 9/1995 | Lindquist | |
| 5,451,442 A | 9/1995 | Pieniak et al. | |
| 5,613,960 A | 3/1997 | Mizutani | |
| 5,795,344 A | 8/1998 | Chappell | |
| 5,807,365 A | 9/1998 | Luceri | |
| 5,865,824 A | * 2/1999 | Chen et al. | 604/378 |
| 5,891,118 A | * 4/1999 | Toyoshima et al. | 604/366 |
| 6,013,065 A | * 11/2000 | Suzuki et al. | 604/385.2 |

FOREIGN PATENT DOCUMENTS

| | | |
|---|---|---|
| EP | 0 903 135 A1 | 3/1999 |
| EP | 1 013 252 A1 | 6/2000 |
| GB | 2 319 730 | 6/1998 |

* cited by examiner

*Primary Examiner*—Dennis Ruhl
*Assistant Examiner*—Jamisue A. Webb
(74) *Attorney, Agent, or Firm*—Caesar, Rivise, Bernstein, Cohen & Pokotilow, Ltd.

(57) ABSTRACT

A disposable absorbent article, e.g., a pantiliner, or other absorbent pad. The pad is an elongated generally planar member having a general hour-glass shape periphery including a pair of concave, side sections interconnecting respective ones of a pair of convex end sections. The pad basically comprises a top-sheet, a fluid absorbent core, and a cover sheet. The top sheet is formed of a fluid pervious material, e.g., a non-woven material, and is disposed over the absorbent core. The absorbent core comprises a fluid absorbing material, e.g., cellulosic fluff and super-absorbent particles, and is disposed over the cover sheet. The cover sheet is formed of a fluid impervious material, e.g., a plastic film. The top-sheet, the fluid absorbent core and the cover sheet are bonded, e.g., thermally bonded, together along plural concentric lines located adjacent the periphery of the pad. The plural concentric lines form a barrier resistant to the egress of fluid out of the periphery of the pad. The concentric lines include gaps therein to facilitate the bending of the pad. The gaps can be located at specific locations in the pad, e.g., between respective ones of adjacent end and side sections, or along the entire length of each of the concentric lines. Moreover, the gaps of one line can be aligned with the gaps of the other lines or the gaps can be staggered.

40 Claims, 5 Drawing Sheets

LIGHT INCONTINENT PRODUCT

FIELD OF THE INVENTION

This invention relates generally to disposable absorbent articles and more specifically to disposable absorbent articles, e.g., light incontinent pads, light menstrual cycle pads, and the like, that are flexible in the interest of comfort while exhibiting enhanced resistance to leakage.

BACKGROUND OF THE INVENTION

Disposable absorbent sanitary articles, e.g., such as pantiliner pads, frequently make use of one or more lines or grooves to deter the egress of liquid out of the article. For example, U.S. Pat. No. 5,807,365 (Luceri) discloses a disposable shield of a generally dog-bone shape comprising a thin, highly absorbent pad having a body-contacting surface, an absorbent layer, a liquid barrier, a positioning adhesive for attaching the pad to an undergarment, and a release layer to protect the adhesive prior to use. The pad further comprises densified areas forming unbroken concentric rings having the same general shape as the shield itself. These rings are made by fusing all pad layers together in a pattern embosser to create densified areas resistant to the flow of liquid therethrough. The densified areas are made contiguous such that fluid, when introduced or deposited on the pad, will be prevented or hindered from flowing to the edges of the pad. Moreover, the concentric rings serve to separate, or compartmentalize, the pad into distinct absorbing areas which are isolated from each other.

U.S. Pat. No. 5,795,344 (Chappell) discloses an absorbent article, such as a sanitary napkin having a cover, a baffle and an absorbent between the cover and baffle and includes a single, unbroken embossed channel positioned inward from the peripheral edge of the article. The channel impedes the flow of fluid toward the edges of the absorbent article and increases absorbent utilization in the absorbent article. The channel can be produced various ways, such as by application of heat, including hot calendar embossing or by using ultrasonic means.

U.S. Pat. No. 5,891,118 (Toyoshima et al) discloses elongated absorbent articles that includes an antileakage groove formed along each longitudinal side portion of the article. The antileakage groove may be continuous or discontinuous and only extends partially into the thickness of the article.

Other United States Patents disclosing absorbent articles or pads with channels, grooves or embossed or debossed lines are: U.S. Pat. No. 4,624,666 (DeRossett et al), U.S. Pat. No. 4,758,240 (Glassman), U.S. Pat. No. 5,104,396 (Oatley et al), U.S. Pat. No. 5,447,506 (Lindquist), U.S. Pat. No. 5,451,442 (Pieniak et al) and U.S. Pat. No. 5,613,960 (Mizutani).

Pantiliners or other sanitary disposable absorbent articles or pads are also commercially available that make use of at least one barrier line to prevent the egress of liquid from a peripheral portion of the article. For example, a "regular maxipad" sold under the trademark FRESH TIMES® by The Kendall Confab Retail Group, a division of the assignee of this invention, basically comprises an hour-glass shaped pad having an outer sheet or cover formed of a fluid-impervious, e.g., plastic, material, an inner liner formed of a fluid-pervious, e.g., non-woven, material, and an absorbent core, e.g., fluff and/or SAP, etc., interposed therebetween. In order to prevent leakage of the liquid which is absorbed through the inner liner into the core, the FRESH TIMES® pad is embossed, e.g., heat sealed, along a broken line generally conforming to the periphery of the pad. The breaks or gaps in the line are provided in the interest of maintaining flexibility of the pad so that it can conform to the crotch area of the wearer. To that end, the embossed line is broken at two points along both of the long sides of the pad spaced from the center of those sides and just at the interface with the ends of the line. The unbroken portions of the embossed line serve as a barrier to prevent the migration of liquid through it and out of either marginal side edge of the pad or out of either marginal end edge of the pad.

While all of the foregoing absorbent articles are suitable for their intended purposes, they never the less leave something to be desired from the standpoint of retention of fluid, (e.g., resistance to leakage) flexibility and conformability to the body of the wearer.

SUMMARY OF THE INVENTION

This invention relates to a disposable absorbent article, e.g., pantiliner or other absorbent pad, arranged to be worn by a wearer to trap and collect fluid waste products of the wearer and a method of making the absorbent article. The pad being an elongated generally planar member having a periphery, e.g., of a general hour-glass shape, including a pair of longitudinal extending, e.g., concave, sides interconnecting respective ones of a pair of ends, e.g., convex ends.

The pad basically comprising a top-sheet, a fluid absorbent core, and a cover sheet. The top sheet is formed of a fluid pervious material, e.g., a non-woven material, and is disposed over the absorbent core. The absorbent core comprises a fluid absorbing material, e.g., cellulosic fluff and super-absorbent particles, and is disposed over the cover sheet. The cover sheet is formed of a fluid impervious material, e.g., a plastic film.

The top-sheet, the fluid absorbent core and the cover sheet are bonded together along plural concentric lines located adjacent the sides and plural concentric lines adjacent the ends, e.g., plural concentric lines which are themselves concentric with the periphery of the pad. The plural concentric lines form a barrier resistant to the egress of fluid out of the periphery of the pad and include at least one gap therein to facilitate the bending of the pad.

In accordance with one aspect of the method the concentric lines are produced by the application of pressure, e.g., thermal bonding, to compress the material of the top-sheet, the fluid absorbent core and the cover sheet together to form a line resistant to the passage of fluid therethrough.

DETAILED DESCRIPTION OF THE PREFERRED EMBODIMENT

Figure 1:
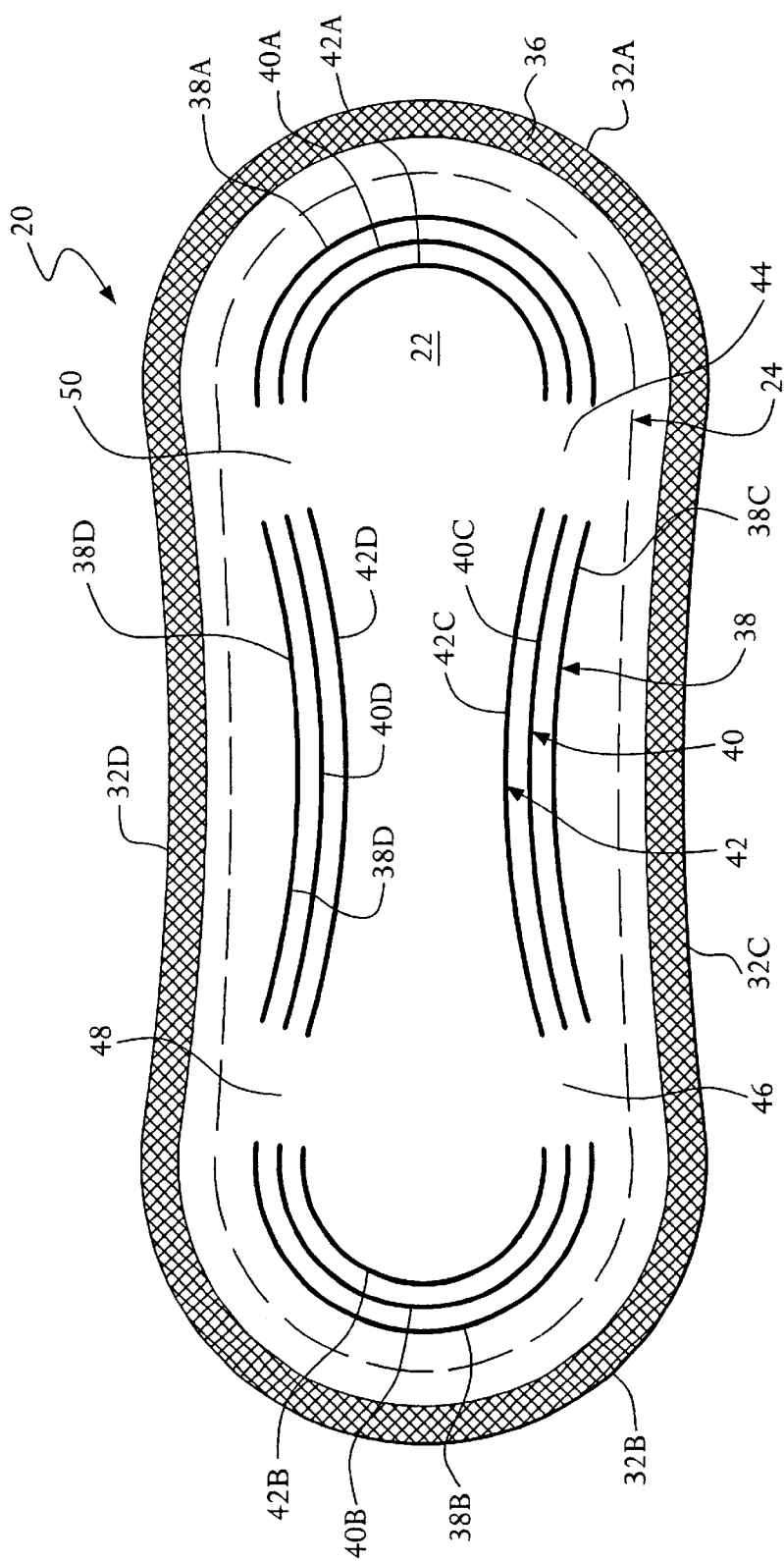
FIG. 1 is a plan view of one preferred embodiment of an absorbent article or pad constructed in accordance with the subject invention.

Referring now to the various figures of the drawing wherein like reference characters refer to like parts, there is shown in FIG. 1 a disposable absorbent article 20 constructed in accordance with one embodiment of this invention. It should be pointed out that as used herein the term "disposable" means that article is designed to be used until soiled, either by urination or otherwise, and then discarded, rather than being washed and used again.

In the embodiment of FIG. 1 the article 20 is in the form of a pantiliner pad. While the following description will focus on pantiliners, it should be clear that the subject invention can be used for any type of pad-like absorbent article to be worn by a person within an undergarment for trapping urine or menses.

Figure 2:
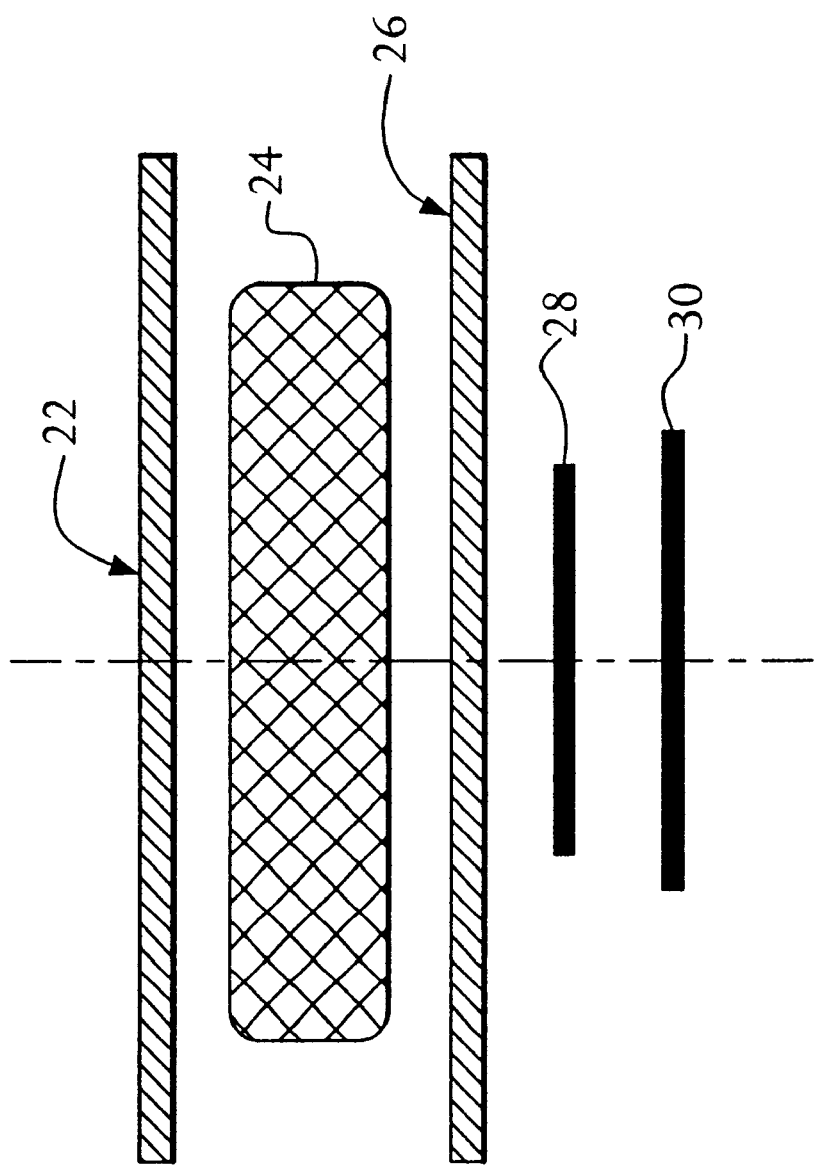
FIG. 2 is an enlarged, exploded, cross sectional view taken along line 2—2 of FIG. 1.

The pantiliner 20 basically comprises a thin generally planar structure. In particular, the pad may be any thickness in the range of 1 mm to 12 mm, with 3.0 mm being one preferred thickness for a pantiliner. As can best be seen in FIG. 2, the pad is formed of a liquid pervious inner liner or layer 22, a liquid absorbent, e.g., air-laid composite, core 24, and an outer cover or moisture barrier 26. The inner layer may be of any liquid pervious material. One particularly suitable material is a 15 gsm wettable nonwoven coverstock, made of spun bond polypropylene, available from BBA Nonwovens. The inner layer 22 is disposed directly on-top of the absorbent core 24 and, if desired may be secured thereon by a low add-on adhesive (not shown). One particularly suitable material for the adhesive is available from National Starch and Chemical of Bridgewater, N.J. under the trade designation 34-5637. The inner layer 22 may be formed of other material fibers (e.g., polyethylene, bi-component, polyester, rayon, cotton, etc.), fiber combinations (e.g., spunbond, air laid, wet laid, carded, hydroentangled, etc.), and basis weights may be used as well. In fact, if desired, the inner layer 22 may be formed of a liquid impermeable material, e.g., three dimensional polymeric film, having plural apertures or pores extending therethrough so as to make the material liquid permeable. One particularly suitable polymeric film is that disclosed in U.S. Design Letters Pat. No. 362,120, which patent is assigned to the same assignee as this invention and whose disclosure is incorporated by reference herein.

The outer layer or moisture barrier 26 is disposed directly over the other side of the absorbent core 24, i.e., on the opposite side from the inner layer 22, and, if desired may be secured thereon by a high add-on adhesive (not shown, like that which may be used to secure the inner layer 22 to the core 24).

The core 24 can be made up of any suitable absorbent material, as well as combinations of different types of absorbent material(s). For example, in one preferred embodiment shown herein the absorbent core 24 is formed of an air-laid absorbent material, such as wood pulp, and which optionally can contain a super absorbent polymer powder (SAP) and a binder. Examples of SAP include polyacrylamides, polyvinyl alcohol, polyacrylates, various grafted starches, and the like. One particularly suitable super absorbent material is a cross-linked polysodium acrylate, which can be purchased from Chemdal Corporation, Palatine, Ill., under the trade designation ASAP 2100.

If desired the pad may include a fluid acquisition or transfer layer (not shown) located between the inner layer 22 and the core 24. As is known a fluid acquisition layer serves to manage, transport, accommodate and/or direct high volumes and flow rates of urine into the core. The fluid acquisition layer can be of any type construction, e.g., a thru-air bonded/carded web, a spunbond bicomponent nonwoven web, a web of crosslink cellulosic fibers, apertured 3D (three dimensional) film or the like.

In order to hold the pad 20 in place within the wearer's undergarment, it includes a stripe 28 (FIG. 2) of a "positioning" adhesive on the outer surface of the moisture barrier 26 extending along the longitudinal central axis of the pad for substantially the length of the pad. Any suitable positioning adhesive can be used for the stripe, such as a pressure sensitive hot melt adhesive. One particularly suitable material for the positioning adhesive 28 is available from National Starch and Chemical of Bridgewater, N.J. under the trade designation 34-5598. In order to protect the positioning adhesive stripe 28 from degradation or being soiled by debris, a single release strip 30 (e.g., a release paper) is releasably secured over the stripe. The release strip 30 can be formed of any suitable adhesive protective, yet easy to release, material. One particularly suitable material for the adhesive release strip 30 is available from DCP Lohja Inc. of Willowbrook, Ill. under the trade designation ESP 39.

As best seen in FIG. 1 the periphery or outer profile of the inner layer 22 and the moisture barrier 26 is of a general "dog-bone" shape having a pair of convex arcuate ends 32A and 32B and a pair of slightly concave arcuate sides 32C and 32D. The inner layer 22 and the moisture barrier 26 are each of the exact same size and are disposed coincident with each other. The core 24 is of the same general shape as the inner layer 22 and the moisture barrier 26, but is slightly smaller in size, and is centered within the confines of the coincident peripheries of the inner layer and moisture barrier. The marginal portions of the inner layer 22 and the moisture barrier 26 which extend beyond the periphery of the core 24 are secured together along their respective inner surfaces by any suitable means, e.g., thermal or ultrasonic bonding, or by an adhesive (not shown) to form a peripheral seal line 36. One particularly suitable material for the adhesive is available from National Starch and Chemical of Bridgewater, N.J., under the trade designation 34-5637.

In accordance with one exemplary embodiment of this invention the longitudinal dimension of the pad, i.e., the maximum distance between the arcuate ends 32A and 32B along the central longitudinal axis is approximately 13 inches (33 cm), whereas the lateral dimension measured transversely across the pad at the center of the longitudinal, i.e., the minimum distance between the arcuate sides 32C and 32D is approximately 2 inches (5 cm).

In order to prevent the migration of liquid, e.g., urine or menses, laterally out of the pad 20, as well as to ensure that such liquid is directed throughout the pad into its core 24 for trapping therein, the pad 20 includes a plurality of concentric barrier lines (to be described later). Each of the concentric barrier lines is arranged to form a somewhat dense wall across which fluid cannot flow, while helping to direct or "channel" the fluid to flow therealong.

As will be appreciated by those skilled in the art from the explanation to follow, the manner of formation of the concentric barrier lines results in the portion of the pad 20 along each line being denser than the contiguous areas of the pad to result in a reduced or restricted flexibility along the line. This factor would render a pad having respective continuous, i.e., unbroken, concentric barrier lines somewhat inflexible and uncomfortable. In order to overcome this characteristic, each concentric barrier line of the subject invention is broken to form at least one gap therein, so that the pad can readily flex or bend at the location of the at least one gap. Moreover, fluid (e.g., urine and/or menses) can flow through the at least one gap from one area of the pad that is bounded by a barrier line into another area of the pad that is bounded by another barrier line, thereby spreading the fluid throughout the core, while the unbroken portions of the concentric barrier lines preclude the egress of the fluid from the periphery of the pad.

In the embodiment 20 shown in FIG. 1 there are three concentric barrier lines 38, 40, and 42. Each of the lines 38, 40 and 42 is of the same general shape as the periphery of the pad 20. Each line includes a pair of convex arcuate end sections and a pair of concave side sections. The end sections of the barrier line 38 are designated by the reference numbers 38A and 38B. The end sections of the barrier line 40 are designated by the reference numbers 40A and 40B, and the end sections of the barrier line 42 are designated by the reference numbers 42A and 42B. The side sections of the barrier line 38 are designated by the reference numbers 38C and 38D. The side sections of the barrier line 40 are designated by the reference numbers 40C and 40D, and the side sections of the barrier line 42 are designated by the reference numbers 42C and 42D.

Each section of each barrier line is produced by applying pressure and/or heat to the portions of the pad along the line to compress and increase the density of the materials along those lines, e.g., to compress the core 24. Depending upon the construction of the pad, the compression and/or heat applied to the materials making up the pad (particularly its core) causes the interstitial space between the individual fibers making up the core (any other layers of the pad composed of fibrous material) to compress or become densified to the point at which such densified areas are insufficient to allow liquid to flow therethrough. The application of pressure and heat can be accomplished using conventional thermal or ultrasonic bonding techniques or by pattern embossing. In some applications the use of pressure alone may be sufficient to produce a dense barrier line which remains after the pressure is removed. Moreover, an adhesive may be used when pressure is applied to create the dense barrier line. In fact, it is contemplated that water can be used in lieu of an adhesive for use with a core of suitable material so that after the pressure is released and the core dries the previously wet and compressed portions of the core will remain compressed, thereby forming the barrier lines.

As will be appreciated by those skilled in the art most leakage from a pad is along the marginal sides along the center portion of the pad. Thus, each of the side sections 38C and 38D of the barrier line 38, each of the side sections 40C and 40D of the barrier line 40, and each of the side sections 42C and 42D of the barrier line 42 extend for a substantial distance along the respective sides 32C and 32D of the pad 20 and are centered along the longitudinal axis of the pad. These relatively long side sections prevent liquid from exiting the pad laterally. The end sections 38A and 38B of the barrier line 38, the end sections 40A and 40B of the barrier line 40, and the end sections 42A and 42B of the barrier line 42 extend for a substantial distance along the respective ends of the pad and are centered about the longitudinal axis of the pad to preclude liquid from gaining egress at the ends of the pad.

A short, e.g., 0.125 inch to 1 inch, gap 44 is located between the ends of the barrier line sections 38A and 38C of line 38, between the ends of the barrier line sections 40A and 40C of line 40, and between the ends of the barrier line sections 42A and 42C of line 42. Another short, e.g., 0.125 inch to 1 inch, gap 46 is located between the ends of the barrier line sections 38B and 38C of line 38, between the ends of the barrier line sections 40B and 40C of line 40, and between the ends of the barrier line sections 42B and 42C of line 42. Still another short, e.g., 0.125 inch to 1 inch, gap 48 is located between the ends of the barrier line sections 38B and 38D of line 38, between the ends of the barrier line sections 40B and 40D of line 40, and between the ends of the barrier line sections 42B and 42D of line 42. Finally, another short, e.g., 0.125 inch to 1 inch, gap 50 is located between the ends of the barrier line sections 38D and 38A of line 38, between the ends of the barrier line sections 40D and 40A of line 40, and between the ends of the barrier line sections 42D and 42A of line 42.

The short gaps 44–50 enable the pad 20 to flex or bend at their respective locations so that the pad can be bent into a generally cup-shaped member from end to end to accommodate the crotch of the wearer when the pad is worn within an undergarment. Moreover, since the barrier lines are concentric, e.g., spaced from each other by approximately 0.24 inch (6 mm) fluid (e.g., urine and/or menses) can flow through the gaps 44–50 from the area bounded by the innermost of the barrier lines, i.e., line 42, into the areas between that line and the intermediated barrier line 40, and through those gaps into the areas between the intermediate line 40 and the outermost of the barrier lines, i.e., line 38, thereby spreading the fluid throughout the core. The unbroken portions of the concentric barrier lines, as described above, serve as a wall across which the fluid cannot flow, thereby precluding the egress of the fluid from the virtually the entire periphery of the pad. In this regard, while there is no barrier wall at the gaps, it is unlikely that any liquid will gain egress from the pad at these locations since they are relatively short in length so that virtually all of the liquid will be trapped in the core of the pad bounded by the unbroken portions of the barrier lines.

Figure 3:
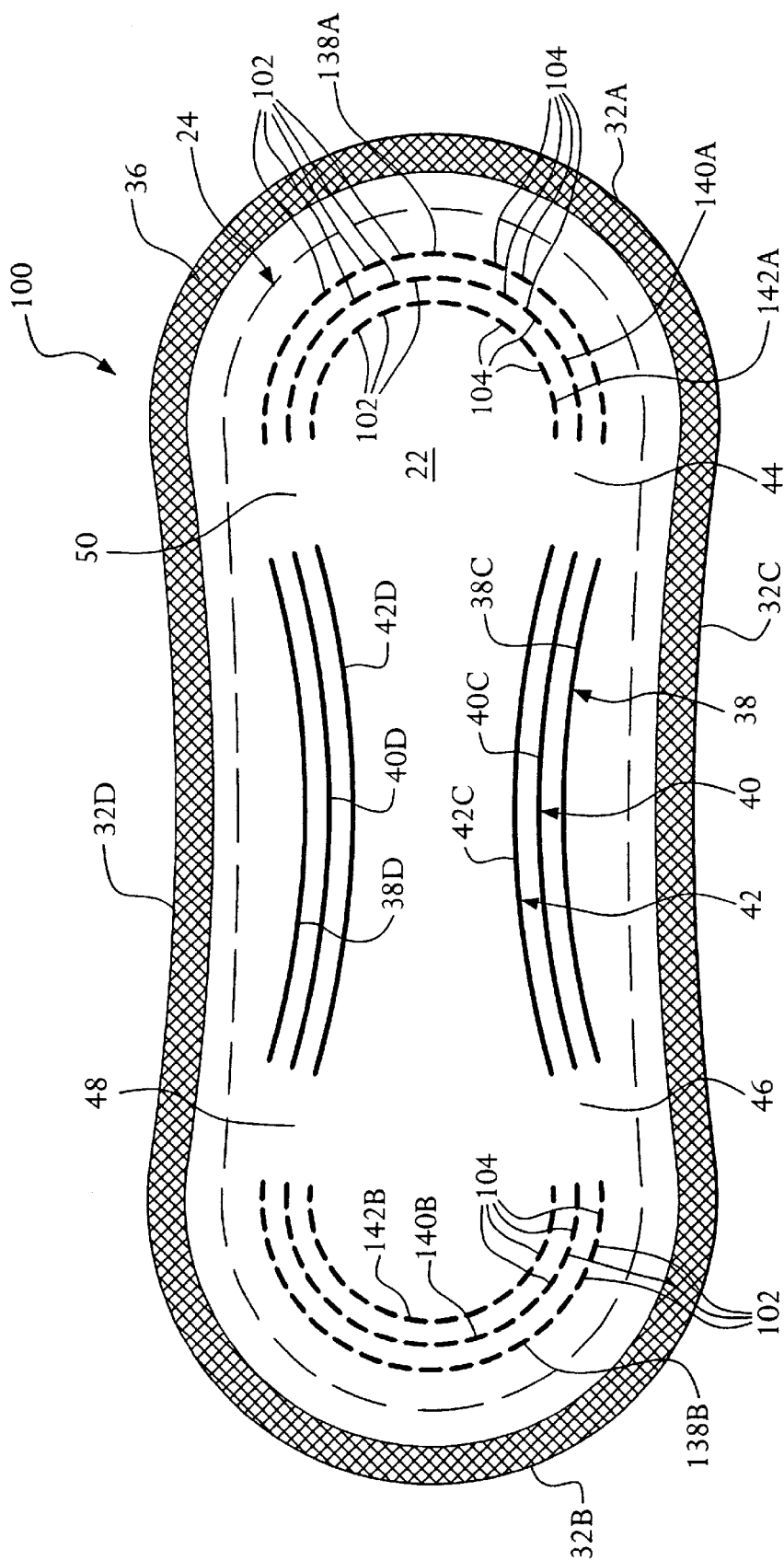
FIG. 3 is a plan view, similar to FIG. 1, but showing an alternative embodiment of an absorbent article or pad constructed in accordance with the subject invention.

In FIG. 3 there is shown an alternative embodiment of a pantiliner pad 100 constructed in accordance with this invention. The pad 100 is identical in construction to the pad 20 described heretofore except for the construction of the end sections of each of its barrier lines. In the interest of brevity the common components of the pads 20 and 100 will be given the same reference numbers and the details of their construction and operation will not be reiterated. Thus, as can be seen the end sections of each of the barrier lines 38, 40 and 42 is in the form of a broken or segmented line. In particular, one end section of the barrier line 38 is in the form of broken line 138A having a plurality of short segments 102 which are spaced from each other by respective very narrow gaps 104. The opposite end section of the barrier line 38 is in the form of a broken line 138B having a plurality of short segments 102 which are spaced from each other by respective very narrow gaps 104. In a similar manner one end section of the barrier line 40 is in the form of broken line 140A having a plurality of short segments 102 which are spaced from each other by respective very narrow gaps 104. The opposite end section of the barrier line 40 is in the form of a broken line 140B having a plurality of short segments 102 which are spaced from each other by respective very narrow gaps 104. So too, one end section of the barrier line 42 is in the form of broken line 142A having a plurality of short segments 102 which are spaced from each other by respective very narrow gaps 104. The opposite end section of the barrier line 42 is in the form of a broken line 142B having a plurality of short segments 102 which are spaced from each other by respective very narrow gaps 104.

The short segments of each of the end sections of the barrier lines are formed in the same manner as the barrier lines 38, 40 and 42 described heretofore and each can be of the same length as the others of that section or can be of different lengths. The segments 102 can be in the range of 0.08 inch (2 mm) to 0.8 inch (20.3 mm). So too, each of the gaps can be of the same length as the others of that section or can be of different lengths. The gaps 102 can be in the range of 0.08 inch (2.0 mm) to 0.8 inch (20.3 mm).

As should be appreciated by those skilled in the art, by providing the short segmented end sections 138A and 138B, 140A and 140B, and 142A and 142B, with the multitude of gaps 104 therein, the end portions of the pad 20 can be quite flexible and readily able to conform to the wearer's anatomy. Moreover, since there is less of a tendency for liquid to gain egress from the pad at its ends, than at its center, the fact that there are broken barrier lines at the ends of the pad should not result in any substantial leakage from the ends, particularly since the end segments 102 will act as a barrier to the egress of liquid and will serve to channel or direct the liquid into other portions of the pad 100.

Figure 4:
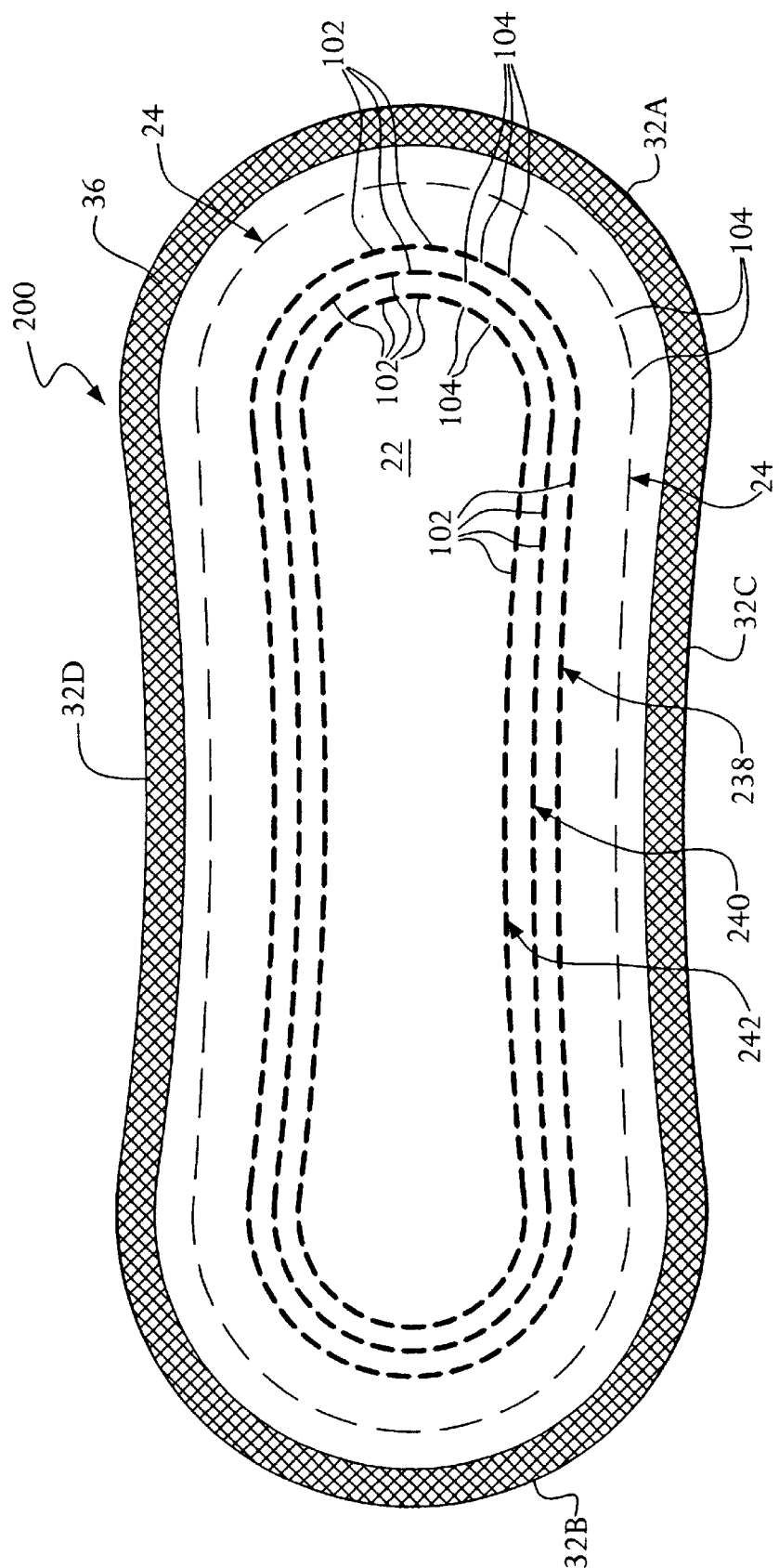
FIG. 4 is a plan view, similar to FIGS. 1 and 3, but showing still another alternative embodiment of an absorbent article or pad constructed in accordance with the subject invention.

In FIG. 4 there is shown another alternative embodiment of a pantiliner pad 200 constructed in accordance with this invention. The pad 200 arranged to be even more flexible than the pads 20 and 100, and is identical in construction to those pads 20 and 100 except for the construction of each of its barrier lines. In the interest of brevity the common components of the pads 20, 100 and 200 will be given the same reference numbers and the details of their construction and operation will not be reiterated. Thus, as can be seen each of the barrier lines 238, 240 and 242 is in the form of a broken or segmented line similar to the end line sections 138A and 138B, 140A and 140B, and 142A and 142B of the pad 100. In particular, the innermost barrier line 242 is in the form of a segmented line having a plurality of short segments 102 which are spaced from each other by respective very narrow gaps 104. The intermediate or middle barrier line 240 is also in the form of broken line having a plurality of short segments 102 which are spaced from each other by respective very narrow gaps 104, while the outermost barrier line 238 is also in the form of broken line having a plurality of short segments 102 which are spaced from each other by respective very narrow gaps 104. Each of the gaps 104 of each concentric barrier line is aligned with a corresponding gap of the immediately adjacent barrier line.

The shape of each of the barrier lines 238, 240 and 242 is of the same general shape as the barrier lines described with reference to pads 20 and 100. Moreover, the short segments of each of the barrier lines 238, 240 and 242 are formed in the same manner as described heretofore and each can be of the same length as the others of that section or can be of different lengths. The segments 102 can be in the range of 0.08 inch (2.0 mm) to 0.8 inch (20.3 mm). So too, each of the gaps can be of the same length as the others of that section or can be of different lengths. The gaps 102 can be in the range of 0.08 inch (2.0 mm) to 0.80 inch (20.3 mm).

As should be appreciated by those skilled in the art, by providing barrier lines of short segments spaced from one another by a multitude of small gaps, particularly where the gaps are aligned with one another as is the case in this embodiment, the resulting pad 200 has the ability to bend or flex readily over virtually its entire length and width, so that it can closely conform to the body of the wearer in the interest of comfort. The fact that the barrier lines are broken along their entire length should not result in any substantial leakage from the pad through them, since the gaps are small and each of the segments 102 will act as a barrier to the egress of liquid and will serve to channel or direct the liquid into other portions of the pad 200.

Figure 5:
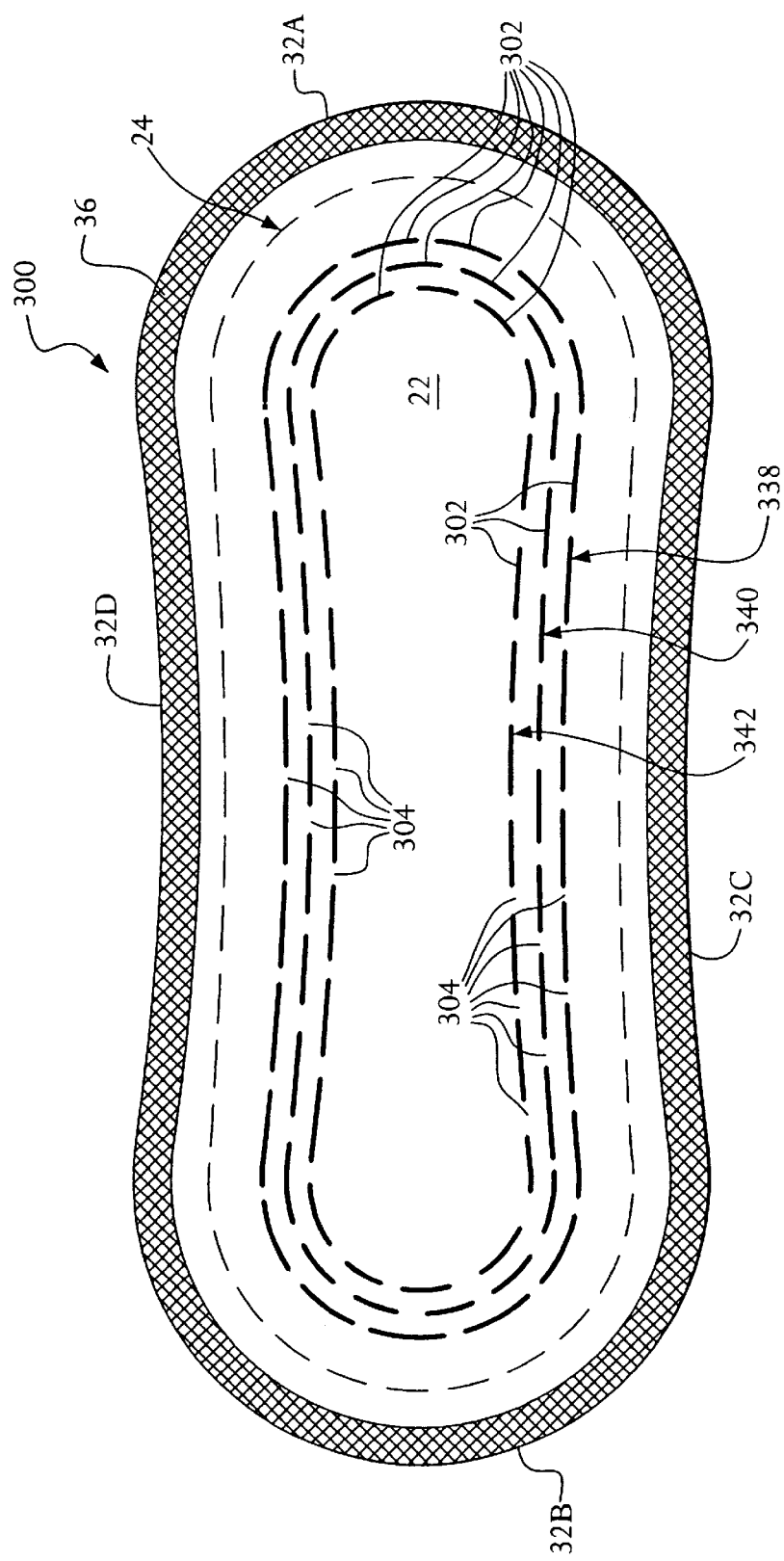
FIG. 5 is a plan view, similar to FIGS. 1, 3 and 4 but showing yet another alternative embodiment of an absorbent article or pad constructed in accordance with the subject invention.

If more leakage protection is desired, without a substantial loss in flexibility, the pad may be constructed in accordance with the embodiment shown in FIG. 5. In particular, in FIG. 5 there is shown another alternative embodiment of a pantiliner pad 300 constructed in accordance with this invention. The pad 300 is identical in construction to the pads 200 except for the construction of each of its barrier lines 338, 340 and 342. In the interest of brevity the common components of the pads 200 and 300 will be given the same reference numbers and the details of their construction and operation will not be reiterated. Thus, as can be seen each of the barrier lines 338, 340 and 342 is in the form a broken line similar to the barrier lines 238, 240 and 242, except that the line segments are somewhat longer in length and the gaps between the segments of one barrier line are offset or staggered from the gaps between the segments of the immediately adjacent barrier line. In particular, the innermost barrier line 342 is in the form of broken line having a plurality of short segments 302 which are spaced from each other by respective very narrow gaps 304. The intermediate or middle barrier line 340 is also in the form of broken line having a plurality of short segments 302 which are spaced from each other by respective very narrow gaps 304, while the outermost barrier line 338 is also in the form of broken line having a plurality of short segments 302 which are spaced from each other by respective very narrow gaps 304. Each of the gaps 304 of each concentric barrier line is offset or staggered with respect to a corresponding gap of the immediately adjacent barrier line, thereby creating a tortuous path through which the liquid in the pad must flow if it is to gain egress from the pad. In particular, any liquid (e.g., urine and/or menses) in the portion of the pad located within the confines of the innermost barrier line 342 can flow through any of its gaps 304 into the space between that line and the intermediate barrier line 340. The liquid will be prevented from flowing radially outward by the presence of the staggered line segments 302 of the intermediate line, so it will have to flow along those line segments. Any liquid which reaches the gaps of the intermediate barrier line 340 can then flow out of those gaps into the space between the intermediate barrier line and the outermost barrier line 338. The liquid will be prevented from flowing radially outward by the presence of the staggered line segments 302 of the outermost barrier line, so it will have to flow along those line segments.

The segments of each of the barrier lines 338,340 and 342 are formed in the same manner as described heretofore and each can be of the same length as the others of that section or can be of different lengths. The segments 302 can be in the range of 0.08 inch (2.0 mm) to 0.80 inch (20.3 mm). So too, each of the gaps can be of the same length as the others of that section or can be of different lengths. The gaps 304 can be in the range of 0.08 inch (2.0 mm) to 0.80 inch (20.3 mm).

As should be appreciated by those skilled in the art, by providing barrier lines of short segments spaced from one another by a multitude of small staggered gaps, the resulting pad 300 has the ability to bend or flex readily over virtually its entire length and width in the interest of comfort, yet will exhibit excellent fluid retention characteristics.

It should be pointed out at this juncture that pads constructed in accordance with this invention can be of various shapes and/or sizes and/or constructions. Moreover, the pads can include any plural number of broken barrier lines, with the shape of those lines being either the same as that of the pad or of different shapes.

Without further elaboration the foregoing will so fully illustrate my invention that others may, by applying current or future knowledge, adopt the same for use under various conditions of service.

I claim:

1. A disposable absorbent pad arranged to be worn by a wearer to trap and collect fluid waste products of the wearer, said pad being an elongated generally planar member having a periphery including a top edge, a bottom edge and a pair of longitudinal extending side edges, said top edge extending generally transversely, said top edge terminating in a pair of top end portions, said bottom edge extending generally transversely, said bottom edge terminating in a pair of bottom end portions, one of said longitudinally extending side edges interconnecting one top end portion and one bottom end portion, the other of said longitudinally extending side edges interconnecting the other top end portion and the other bottom end portion, said pad comprising a top-sheet, a fluid absorbent core, and a cover sheet, said top sheet being formed of a fluid pervious material and being disposed over said absorbent core, said absorbent core comprising a fluid absorbing material and being disposed over said cover sheet, said cover sheet being formed of a fluid impervious material, said top-sheet, said fluid absorbent core and said cover sheet being bonded together along plural concentric lines, portions of said plural concentric lines being located adjacent said sides and portions of said plural concentric lines being located adjacent said top and bottom edges, said plural concentric lines forming a barrier resistant to the egress of fluid out of the periphery of said pad, each of said plural concentric lines including at least one elongate line segment and at least one gap, said at least one elongate line segment having a length extending along a longitudinal axis and a width extending along a transverse axis, said length of said at least one elongate line segment being substantially larger than said width of said at least one elongate line segment said at least one gap serving to enhance the flexibility of said pad at the location of said at least one gap.

2. The pad of claim 1 wherein said periphery of said pad is of a generally hour-glass shape.

3. The pad claim 1 wherein each of said concentric lines is concentric with the periphery of said pad.

4. The pad of claim 1 wherein said top sheet is selected from the group consisting of spun bonded or carded web non-woven materials or apertured three dimensional plastic film.

5. The pad of claim 1 wherein said fluid absorbent core comprises cellulosic fibers.

6. The pad of claim 5 wherein said fluid absorbent core additionally comprises absorption enhancing materials.

7. The pad of claim 1 wherein said cover sheet is formed of a plastic material.

8. The pad of claim 7 wherein said plastic material is selected from the group consisting of polypropylene, polyester, polyethylene, and blends thereof.

9. The pad of claim 1 wherein each of the concentric lines includes a pair of opposed convex arcuate line end sections and a pair of opposed side sections, one of said pair of convex arcuate line end sections being located adjacent one of said pair of ends of said pad, the other of said pair of convex arcuate line end sections being located adjacent the other of said pair of ends of said pad, one of said pair of side sections being located adjacent one of said pair of longitudinally extending sides and the other of said pair of side sections being located adjacent the other of said pair of longitudinally extending sides.

10. The pad of claim 9 wherein said side sections of said concentric lines include a multitude of gaps extending therealong.

11. The pad of claim 9 wherein said side sections of said concentric lines include a multitude of gaps extending therealong and wherein said end sections of said concentric lines include a multitude of gaps extending therealong.

12. The pad of claim 11 wherein the gaps of each of said lines are staggered.

13. The pad of claim 11 wherein the gaps of each of said lines are aligned.

14. The pad of claim 9 wherein each of said concentric lines includes four gaps, with each of said gaps being located between a respective side section and end section.

15. The pad of claim 14 wherein the gaps of each of said lines are aligned.

16. The pad of claim 14 wherein the gaps of each of said lines are staggered.

17. The pad of claim 9 wherein said concentric lines of said end sections includes a multitude of gaps extending therealong.

18. The pad of claim 17 wherein the gaps of each of said lines are aligned.

19. The pad of claim 17 wherein the gaps of each of said lines are staggered.

20. A method of making a disposable absorbent article arranged to be worn by a wearer to trap and collect fluid waste products of the wearer, said method comprising the steps of:

(A) providing a pad having a periphery including a top edge, a bottom edge and a pair of longitudinal extending side edges, said top edge extending generally transversely, said top edge terminating in a pair of top end portions, said bottom edge extending generally transversely, said bottom edge terminating in a pair of bottom end portions, one of said longitudinally extending side edges interconnecting one top end portion and one bottom end portion, the other of said longitudinally extending side edges interconnecting the other top end portion and the other bottom end portion, said pad comprising a top-sheet, a fluid absorbent core, and a cover sheet, said top sheet being formed of a fluid pervious material and disposed over said absorbent core, said absorbent core comprising a fluid absorbing material and being disposed over said cover sheet, and said cover sheet being formed of a fluid impervious material; and (B) bonding said top-sheet, said fluid absorbent core, and said cover sheet together along plural concentric lines located adjacent said sides and said top and bottom edges to form a barrier resistant to the egress of fluid through said lines and out of the periphery of said pad, each of said plural concentric lines including at least one elongate[d] line segment and at least one gap, said at least one elongate line segment having a length extending along a longitudinal axis and a width extending along a transverse axis, said length of said at least one elongate line segment being substantially larger than said width of said at least one elongate line segment said at least one gap serving to enhance the flexibility of said pad at the location of said at least one gap.

21. The method of claim 20 wherein said periphery of said pad is generally hour-glass shaped.

22. The method of claim 20 wherein each of said concentric lines is concentric with the periphery of said pad.

23. The method of claim 20 wherein said top sheet is selected from the group consisting of spun bonded or carded web non-woven materials or apertured three dimensional plastic film.

24. The method of claim 20 wherein said fluid absorbent core comprises cellulosic fibers.

25. The method of claim 20 wherein said fluid absorbent core additionally comprises absorption enhancing materials.

26. The method of claim 20 wherein said concentric lines are produced by the application of pressure to compress the material of said top-sheet, said fluid absorbent core and said cover sheet together, whereupon each of said lines is resistant to the passage of fluid therethrough.

27. The method of claim 26 wherein said concentric lines are produced by thermally bonding said top-sheet, said fluid absorbent core and a cover sheet together.

28. The method of claim 20 wherein said cover sheet is formed of a plastic material.

29. The method of claim 28 wherein said plastic material is selected from the group consisting of polypropylene, polyester, polyethylene, and blends thereof.

30. The method of claim 20 wherein each of the concentric lines includes a pair of opposed convex arcuate line end sections and a pair of opposed side sections, one of said pair of convex arcuate line end sections being located adjacent one of said pair of ends of said pad, the other of said pair of convex arcuate line end sections being located adjacent the other of said pair of ends of said pad, one of said pair of side sections being located adjacent one of said pair of longitudinally extending sides and the other of said pair of side sections being located adjacent the other of said pair of longitudinally extending sides.

31. The method of claim 30 wherein said side sections of said concentric lines include a multitude of gaps extending therealong and wherein said end sections of said concentric lines include a multitude of gaps extending therealong.

32. The method of claim 31 wherein the gaps of each of said lines are aligned.

33. The method of claim 31 wherein the gaps of each of said lines are staggered.

34. The method of claim 30 wherein said concentric lines of said end sections includes a multitude of gaps extending therealong.

35. The method of claim 34 wherein the gaps of each of said lines are aligned.

36. The method of claim 34 wherein the gaps of each of said lines are staggered.

37. The method of claim 35 wherein each of said concentric lines includes four gaps, with each of said gaps being located between a respective side section and end section.

38. The method of claim 30 wherein said side sections of said concentric lines include a multitude of gaps extending therealong.

39. The method of claim 38 wherein the gaps of each of said lines are aligned.

40. The method of claim 38 wherein the gaps of each of said lines are staggered.

* * * * *